(12) United States Patent
Al-Massarani et al.

(10) Patent No.: US 9,974,750 B1
(45) Date of Patent: May 22, 2018

(54) SYNTHESIS OF IFFLAIONIC ACID NANOPARTICLES

(71) Applicant: KING SAUD UNIVERSITY, Riyadh (SA)

(72) Inventors: Shaza Mohamed Adel Al-Massarani, Riyadh (SA); Rabab Abd El Moneim Khalil El Dib, Riyadh (SA); Ali Ali El-Gamal, Riyadh (SA); Manal Ahmed Gasmelseed, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days. days.

(21) Appl. No.: 15/785,277

(22) Filed: Oct. 16, 2017

(51) Int. Cl.
*A61K 9/19* (2006.01)
*A61K 31/56* (2006.01)

(52) U.S. Cl.
CPC .............. *A61K 9/19* (2013.01); *A61K 31/56* (2013.01)

(58) Field of Classification Search
None
See application file for complete search history.

(56) References Cited

U.S. PATENT DOCUMENTS

| | | |
|---|---|---|
| 7,083,814 B2 | 8/2006 | Ilic et al. |
| 8,168,835 B2 | 5/2012 | Uang et al. |
| 2013/0012470 A1 | 1/2013 | Colman et al. |
| 2015/0093371 A1 | 4/2015 | Colman et al. |

OTHER PUBLICATIONS

Moniruzzaman et al., "Evaluation of Sedative and Hypnotic Activity of Ethanolic Extract of Scoparia dulcis Linn" Evidence-Based Complementary and Alternative Medicine, 2015, vol. 2015, Article ID 873954, 6 pages.
Al-Massarani, "New Cytotoxic Seco-Type Triterpene and Labdane-Type Diterpenes from Nuxia oppositifolia," Molecules 2017, vol. 22, pp. 389.
Hayashi, M. Kawasaki et al., "Antiviral agents of plant origin. III. Scopadulin, a novel tetracyclic diterpene from Scoparia dulcis L.," Chemical and Pharmaceutical Bulletin, 1990, vol. 38, No. 4, pp. 945-947.

*Primary Examiner* — Susan T Tran
(74) *Attorney, Agent, or Firm* — Richard C. Litman

(57) ABSTRACT

Synthesis of ifflaionic acid nanoparticles includes dissolving a powder of ifflaionic acid in an alcohol solution to form a first solution, adding the first solution to an aqueous solution under ultrasonic conditions to produce a sonicated solution, stirring the sonicated solution for a duration of time to produce a mixture, and freeze-drying the mixture to provide the ifflaionic acid nanoparticles.

5 Claims, 6 Drawing Sheets

SYNTHESIS OF IFFLAIONIC ACID NANOPARTICLES

BACKGROUND OF THE INVENTION

1. Field of the Invention

The present invention relates to nanoparticle synthesis, and particularly to synthesis of ifflaionic acid nanoparticles.

2. Description of the Related Art

Nanotechnology has revolutionized various fields of medicine, agriculture, environment and electronics. Nanoparticles exhibit completely new or improved properties compared to their corresponding bulk materials. For example, nanoparticles possess a very high surface to volume ratio. As such, they are particularly useful in applications where high surface areas are critical for success.

In recent years, new synthesis methodologies have facilitated numerous applications in various fields. Nanoparticles can be synthesized from chemical or natural products. Nanoparticle synthesis from natural products is usually more preferable. When compared to nanoparticles manufactured from chemicals, for example, nanoparticles made from natural products are more eco-friendly, readily available, cost effective, and have little if any side effects.

SUMMARY OF THE INVENTION

Synthesis of ifflaionic acid nanoparticles includes dissolving a powder of ifflaionic acid in an alcohol solution to form a first solution, adding the first solution to an aqueous solution under ultrasonic conditions to produce a sonicated solution, stirring the sonicated solution for a duration of time to produce a mixture, and freeze-drying the mixture to provide the ifflaionic acid nanoparticles. The ifflaionic acid (3-oxours-12-en-30-oic acid) can be obtained from the aerial parts of *Nuxia oppositifolia*, These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Synthesis of ifflaionic acid nanoparticles includes dissolving a powder of ifflaionic acid in an alcohol solution to form a first solution, adding the first solution to an aqueous solution under ultrasonic conditions to produce a sonicated solution, stirring the sonicated solution for a duration of time to produce a mixture, and freeze-drying the mixture to provide the ifflaionic acid nanoparticles. The alcohol solution can include methanol and/or ethanol. The aqueous solution can be water. The water can be boiled prior to addition of the alcohol solution. The alcohol solution can be added dropwise to the boiled water at a flow rate of, for example, about 0.2 ml/min to about 0.4 ml/min for about 10 minutes. Sonication can last for about 20 minutes. The sonicated solution can be stirred for about 15 minutes.

Figure 1:
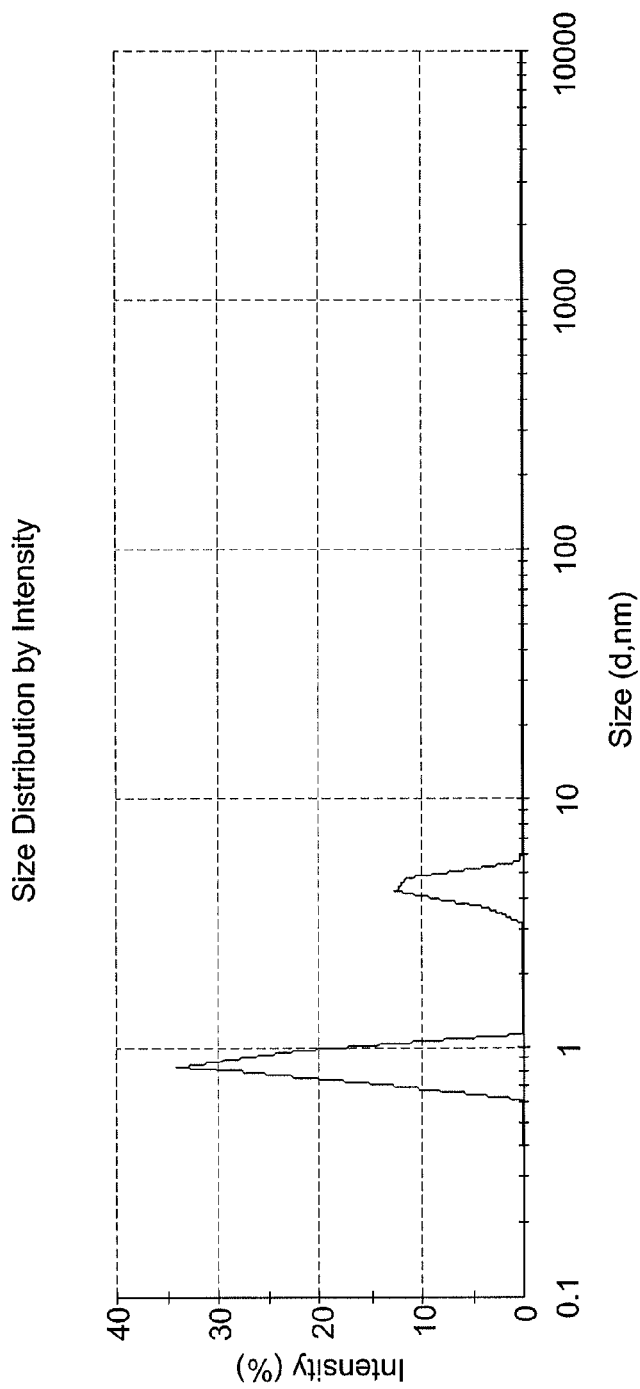
FIG. 1 is a graph showing the particles size distribution of ifflaionic acid nanoparticles (10-100 nm) synthesized according to the present invention.
Figure 2A:
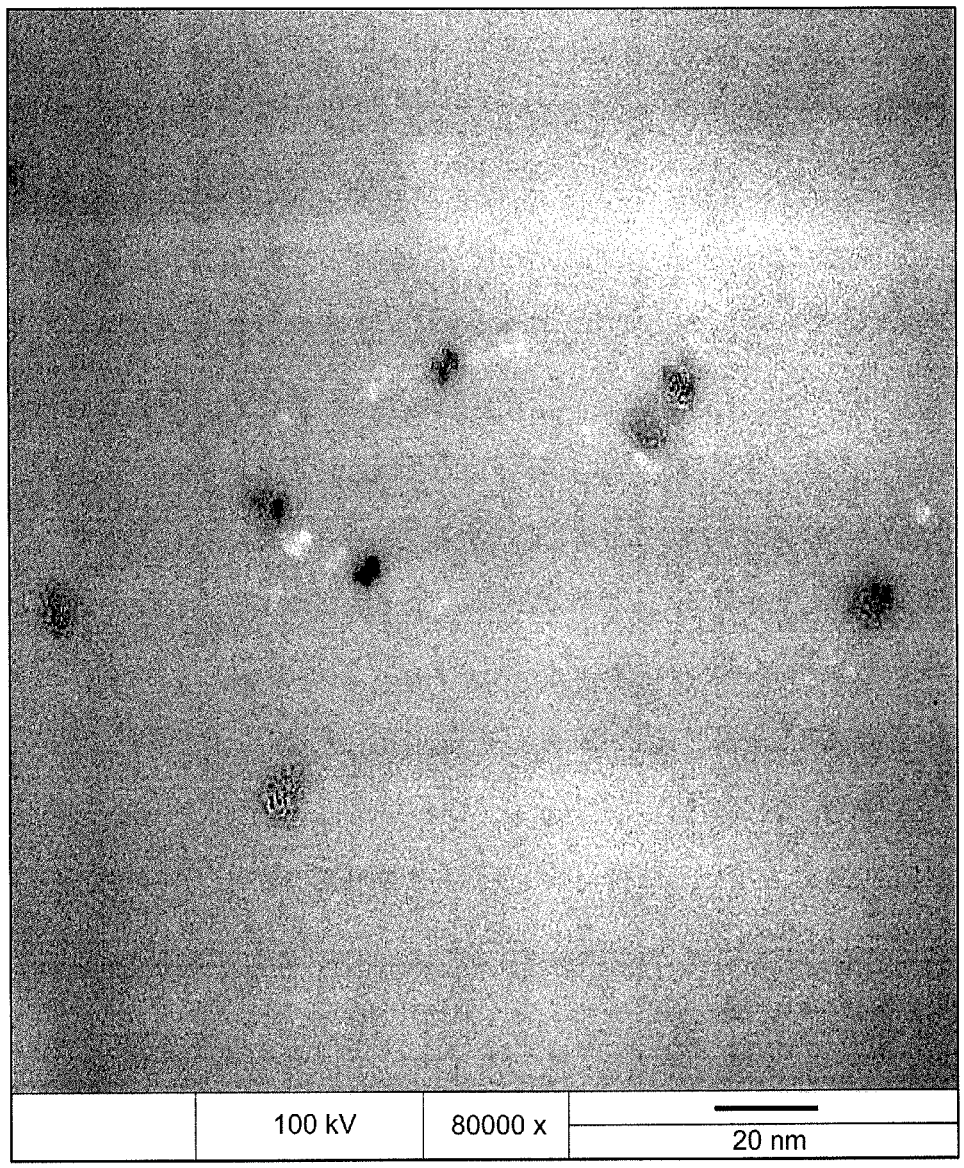
FIGS. 2A-2B are TEM images of the ifflaionic acid nanoparticles synthesized according to the present invention.
Figure 2B:
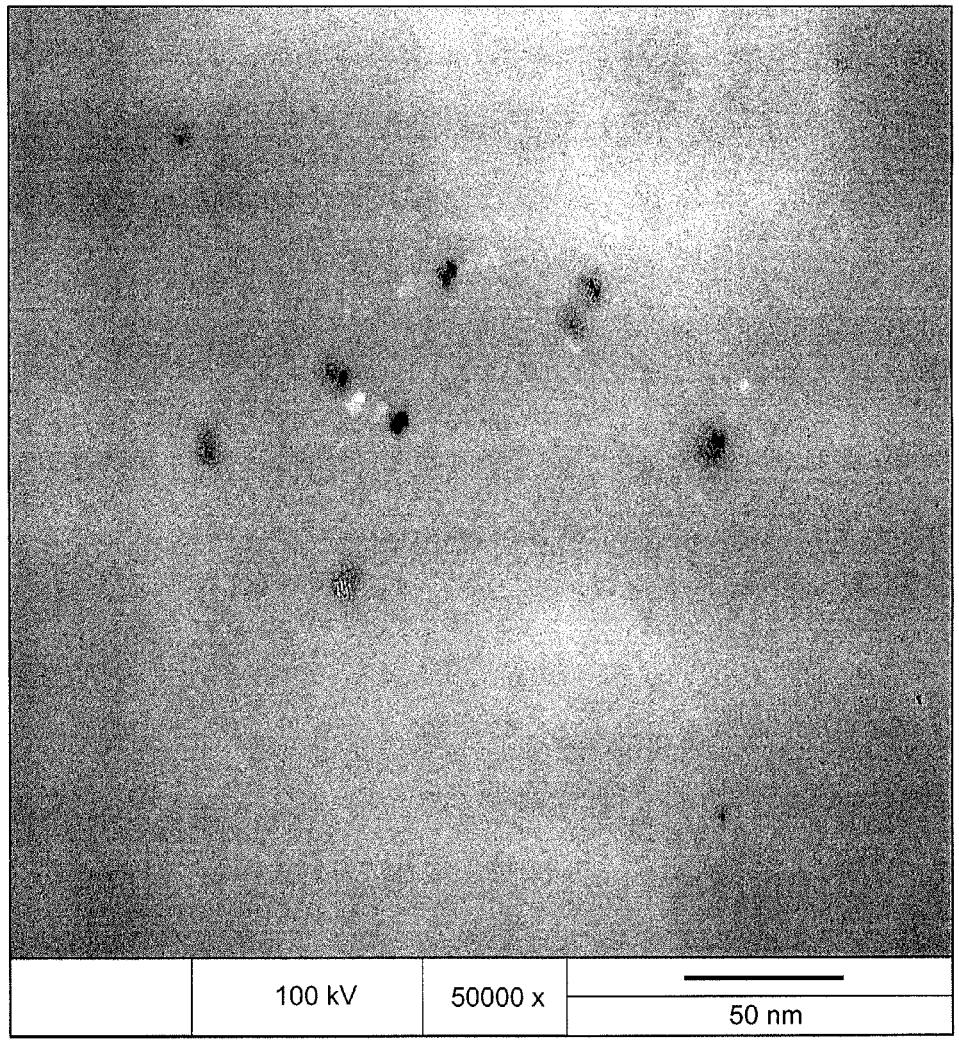

As shown in FIGS. 1 and 2A-2B, the ifflaionic acid nanoparticles can range in size from about 0.5 nm to about 10 nm. The nanoparticles can have an average diameter of about 1 nm.

Figure 3:
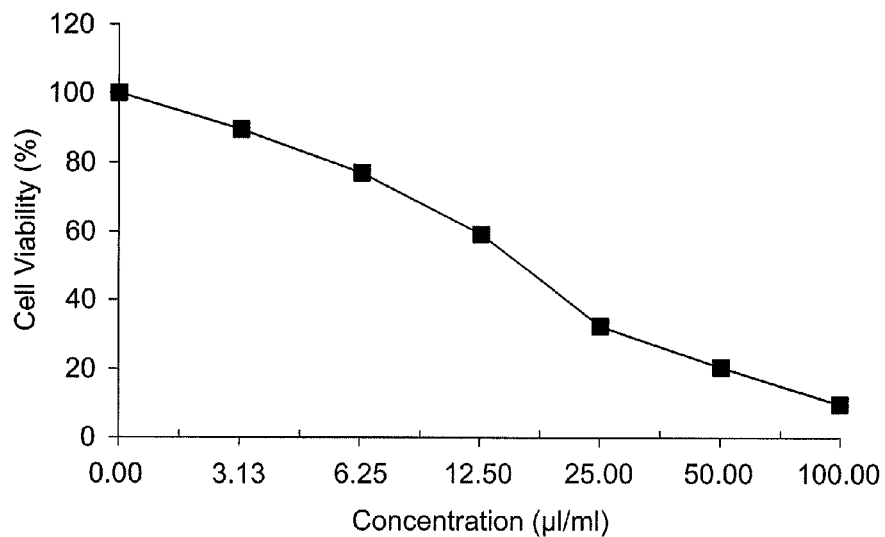
FIG. 3 is a graph showing the cytotoxicity of the ifflaionic acid nanoparticles synthesized according to the present invention against MCF-7 cell line.
Figure 4:
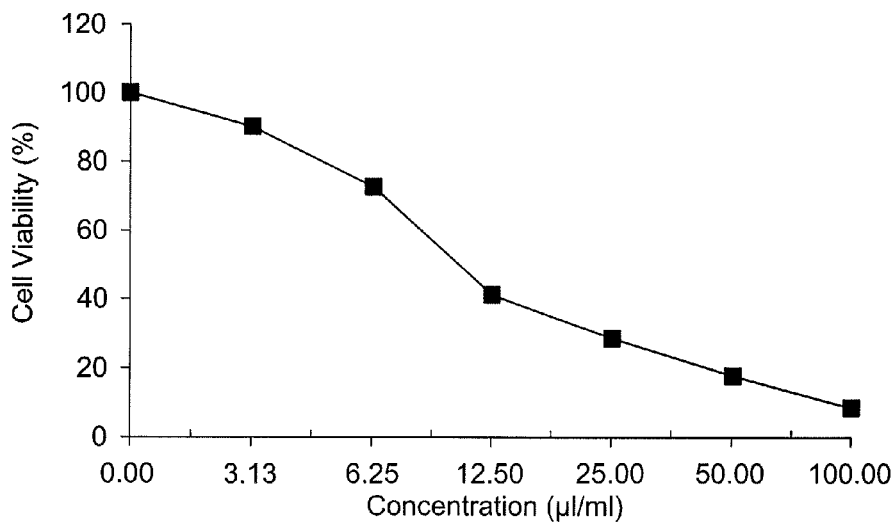
FIG. 4 is a graph showing the cytotoxicity of the ifflaionic acid nanoparticles synthesized according to the present invention against HepG-2 cell line.
Figure 5:
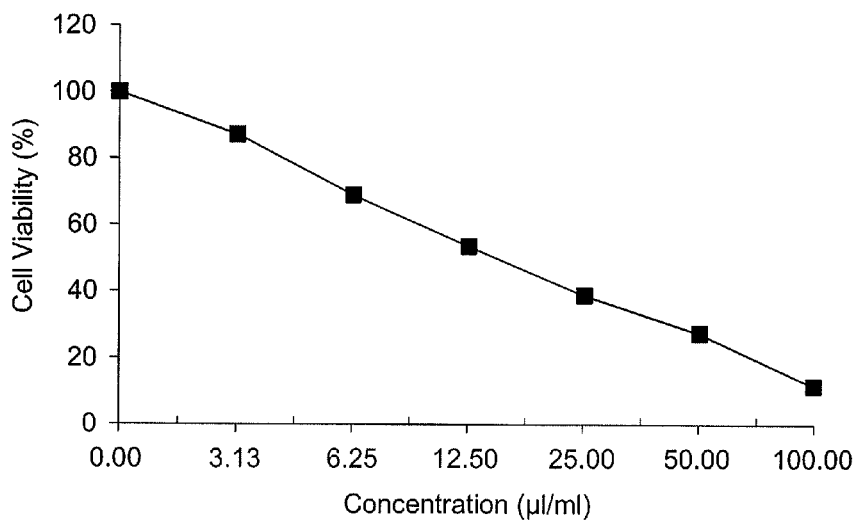
FIG. 5 is a graph showing the cytotoxicity of the ifflaionic acid nanoparticles synthesized according to the present invention against HCT-116 cell line.
Figure 6:
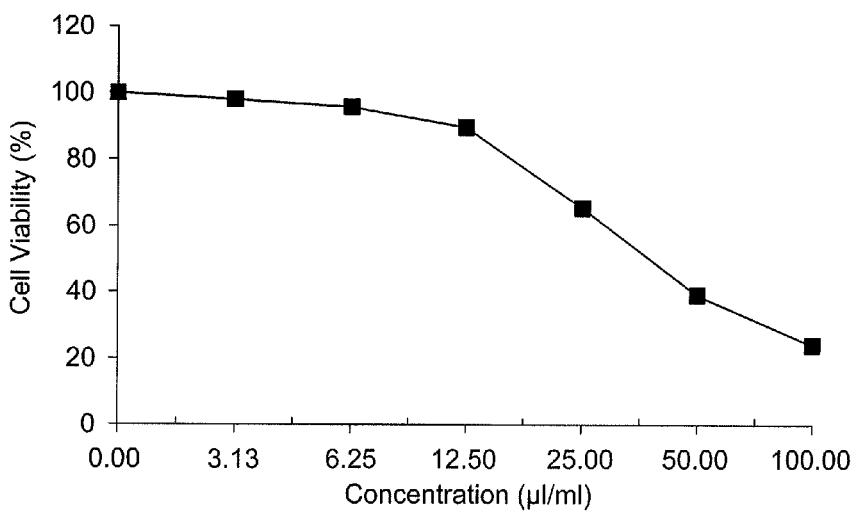
FIG. 6 is a graph showing the cytotoxicity of the ifflaionic acid nanoparticles synthesized according to the present invention against A-549 cell line.
Figure 7:
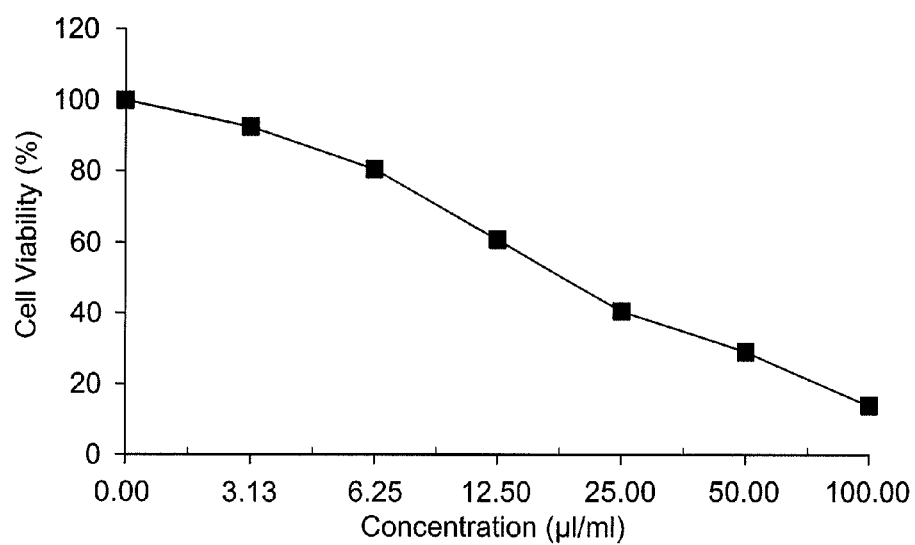
FIG. 7 is a graph showing the cytotoxicity of the ifflaionic acid nanoparticles synthesized according to the present invention against Hela cell line.

The ifflaionic acid nanoparticles possess potent antitumor properties and are effective in inhibiting cancer cells. For example, the ifflaionic acid nanoparticles demonstrated inhibition of breast carcinoma cells (FIG. 3), hepatocellular carcinoma cells (FIG. 4), human colon carcinoma cells (FIG. 5), human lung adenocarcinoma epithelial cells (FIG. 6), and cervical carcinoma cells (FIG. 7). The ifflaionic acid nanoparticles also demonstrated antimicrobial properties.

Ifflaionic acid (3-oxours-12-en-30-oic acid) can be obtained from the aerial parts of *Nuxia oppositifolia*, the bark and leaves of *Flindersia ifflaiana*, and/or the bark and leaves of *Scoparia dulcis*. For example, ifflaionic acid can be obtained from the n-hexane fraction of the aerial parts of *Nuxia oppositifolia* using chromatographic purification techniques.

The following examples illustrate the present teachings.

Example 1

Synthesis of Ifflaionic Acid Nanoparticles

The compound 3-oxours-12-en-30-oic acid (ifflaionic acid) was obtained from the n-hexane fraction of the aerial parts of the Saudi plant *Nuxia oppositifolia*, following a number of chromatographic purification techniques. The structure was identified by different spectroscopic methods, including IR and 1 and 2-D NMR and by comparison with published data. The acid has previously been isolated for the bark and the leaves of *Flindersia ifflaiana* and from *Scoparia dulcis* (Bosson et al., 1963; Chiu-Ming C and Ming-Tyan C, 1976)

The powder of ifflaionic acid (50 mg) was dissolved in 10 mL of methanol and ethanol to form a solution designated "solution A". Water (50 ml) was boiled, and then 5 ml of solution A were added dropwise into the boiled water, with a flow rate of 0.2-0.4 ml/min in 10 minutes, under ultrasonic conditions. After sonication for 20 min, the content was stirred for about 15 minutes, and then freeze-dried.

The synthesized nanoparticles were characterized using Zetasizer, Nano series, HT Laser, ZEN3600 from Molvern Instrument, UK to determine the average size of the resulting nanoparticles. Transmission electron microscopy (TEM, JEM-1400, JEOL, Japan) was employed to characterize the size, shape and morphologies of nanoparticles. FIG. 1 shows the particle size distribution of the ifflaionic acid nanoparticles, with the Z-average particle size being 1.222 nm. FIGS. 2A-2B show TEM images of the ifflaionic acid nanoparticles.

Example 2

Cytotoxicity Evaluation of Ifflaionic Acid Nanoparticles

The cytotoxic effects of the synthesized nanoparticles were evaluated against five cancer cell lines, namely breast cancer cells MCF-7 (FIG. 3, Table 1), hepatocellular carcinoma cells HepG-2 (FIG. 4, Table 2), human colon carcinoma cells HCT-116 (FIG. 5, Table 3), human lung adenocarcinoma epithelial cells A549 (FIG. 6, Table 4) and cervical carcinoma cells HeLa (FIG. 7, Table 5). The results, provided in Tables 1-5 and FIGS. 3-7, indicate that the ifflaionic acid nanoparticles synthesized according to the present teachings are effective in inhibiting cancer cells.

TABLE 1

Inhibitory activity of Ifflaionic acid nanoparticles against MCF-7 cells, with $IC_{50} = 17$ μl/ml.

| Sample conc. (μl/ml) | % Viability (3 Replicates) | | | Mean | % Inhibition | Standard Deviation (±) |
|---|---|---|---|---|---|---|
| | $1^{st}$ | $2^{nd}$ | $3^{rd}$ | | | |
| 100 | 9.82 | 8.95 | 10.79 | 9.85 | 90.15 | 0.92 |
| 50 | 24.79 | 17.63 | 19.68 | 20.70 | 79.30 | 3.69 |
| 25 | 36.04 | 31.27 | 30.86 | 32.72 | 67.28 | 2.88 |
| 12.5 | 58.89 | 64.03 | 55.94 | 59.62 | 40.38 | 4.09 |
| 6.25 | 73.56 | 82.31 | 76.45 | 77.44 | 22.56 | 4.46 |
| 3.125 | 87.14 | 91.42 | 90.83 | 89.80 | 10.20 | 2.32 |

TABLE 2

Inhibitory activity of Ifflaionic acid nanoparticles against HepG-2 cells, with $IC_{50} = 10.8$ μl/ml.

| Sample conc. (μl/ml) | % Viability (3 Replicates) | | | Mean | % Inhibition | Standard Deviation (±) |
|---|---|---|---|---|---|---|
| | $1^{st}$ | $2^{nd}$ | $3^{rd}$ | | | |
| 100 | 8.17 | 7.83 | 9.45 | 8.48 | 91.52 | 0.85 |
| 50 | 16.28 | 19.42 | 18.63 | 18.11 | 81.89 | 1.63 |
| 25 | 27.36 | 30.65 | 28.52 | 28.84 | 71.16 | 1.67 |
| 12.5 | 39.81 | 42.36 | 41.74 | 41.30 | 58.70 | 1.33 |
| 6.25 | 64.15 | 76.29 | 78.61 | 73.02 | 26.98 | 7.77 |
| 3.125 | 87.34 | 90.67 | 93.82 | 90.61 | 9.39 | 3.24 |

TABLE 3

Inhibitory activity of Ifflaionic acid nanoparticles against HCT-116 cells, with $IC_{50} = 15.7$ μl/ml.

| Sample conc. (μl/ml) | % Viability (3 Replicates) | | | Mean | % Inhibition | Standard Deviation (±) |
|---|---|---|---|---|---|---|
| | $1^{st}$ | $2^{nd}$ | $3^{rd}$ | | | |
| 100 | 10.29 | 14.06 | 10.64 | 11.66 | 88.34 | 2.08 |
| 50 | 29.82 | 24.95 | 27.83 | 27.53 | 72.47 | 2.45 |
| 25 | 37.67 | 38.18 | 41.32 | 39.06 | 60.94 | 1.98 |
| 12.5 | 53.82 | 56.79 | 50.68 | 53.76 | 46.24 | 3.06 |
| 6.25 | 65.93 | 69.84 | 71.37 | 69.05 | 30.95 | 2.81 |
| 3.125 | 89.78 | 84.65 | 88.02 | 87.48 | 12.52 | 2.61 |

TABLE 4

Inhibitory activity of Ifflaionic acid nanoparticles against A549 cells, with $IC_{50} = 39.8$ μl/ml.

| Sample conc. (μl/ml) | % Viability (3 Replicates) | | | Mean | % Inhibition | Standard Deviation (±) |
|---|---|---|---|---|---|---|
| | $1^{st}$ | $2^{nd}$ | $3^{rd}$ | | | |
| 100 | 26.37 | 21.68 | 24.53 | 24.19 | 75.81 | 2.36 |
| 50 | 40.53 | 36.82 | 39.61 | 38.99 | 61.01 | 1.93 |
| 25 | 69.42 | 61.37 | 66.79 | 65.86 | 34.14 | 4.10 |
| 12.5 | 90.68 | 88.14 | 91.46 | 90.09 | 9.91 | 1.74 |
| 6.25 | 97.14 | 96.75 | 95.04 | 96.31 | 3.69 | 1.12 |
| 3.125 | 98.72 | 100 | 96.72 | 98.48 | 1.52 | 1.65 |

TABLE 5

Inhibitory activity of Ifflaionic acid nanoparticles against Hela cells, with $IC_{50} = 19.2$ μl/ml.

| Sample conc. (μl/ml) | % Viability (3 Replicates) | | | Mean | % Inhibition | Standard Deviation (±) |
|---|---|---|---|---|---|---|
| | $1^{st}$ | $2^{nd}$ | $3^{rd}$ | | | |
| 100 | 15.95 | 13.24 | 12.87 | 14.02 | 85.98 | 1.68 |
| 50 | 31.74 | 30.95 | 24.61 | 29.10 | 70.90 | 3.91 |
| 25 | 40.89 | 43.26 | 37.86 | 40.67 | 59.33 | 2.71 |
| 12.5 | 62.37 | 58.96 | 61.42 | 60.92 | 39.08 | 1.76 |
| 6.25 | 81.95 | 80.42 | 79.23 | 80.53 | 19.47 | 1.36 |
| 3.125 | 94.28 | 93.17 | 89.84 | 92.43 | 7.57 | 2.31 |

Example 3

Antimicrobial Activity Evaluation of Ifflaionic Acid Nanoparticles

The antimicrobial effect of ifflaionic acid nanoparticles were evaluated against gram positive bacteria, gram negative bacteria, as well as fungi. Results of the antimicrobial effect of the nanoparticles are provided in Table 6.

TABLE 6

Antimicrobial activity of synthesized Ifflaionic acid nanoparticles

| | Sample | |
|---|---|---|
| Tested microorganisms | Zone of Inhibition (±SD) | Reference Drug |
| FUNGI | | Amphotericin B |
| *Absidia corymbifera* (RCMB 02564) | 16 ± 0.19 | 23.0 ± 0.10 |
| *Geotricum candidum* (RCMB 05097) | 17 ± 0.24 | 27.0 ± 0.20 |
| *Candida albicans* (RCMB 05036) | 15.3 ± 0.13 | 25.7 ± 0.10 |
| Gram Positive Bacteria | | Ampicillin |
| *Staphylococcus aureus* (RCMB 010027) | 20.3 ± 0.43 | 27.3 ± 0.14 |
| *Staphylococcus epidermidis* (RCMB 010024) | 21.6 ± 0.54 | 25.0 ± 0.18 |
| *Streptococcus pyogenes* (RCMB 010015) | 18.6 ± 0.22 | 26.3 ± 0.34 |
| Gram Negative Bacteria | | Gentamycin |
| *Proteous vulgaris* (RCMB 010085) | 17 ± 0.43 | 23.4 ± 0.30 |
| *Klebsiella pneumoniae* (RCMB 0010093) | 16.6 ± 0.67 | 26.4 ± 0.15 |
| *Salmonella enteritidis* (RCMB 010084) | 19 ± 0.15 | 25.2 ± 0.18 |

* The test was done using diffusion agar technique, well diameter: 6.0 mm; 100 μl was tested; Data are expressed in the form of mean ± S.D.

It is to be understood that the present invention is not limited to the embodiments described above, but encompasses any and all embodiments within the scope of the following claims.

We claim:

1. A method of synthesizing ifflaionic acid nanoparticles, comprising:
   dissolving a powder of ifflaionic acid in an alcohol solution to form a first solution;
   adding the first solution to an aqueous solution under ultrasonic condition to produce a sonicated solution;
   stirring the sonicated solution for a duration of about 15 minutes to produce a mixture; and
   freeze-drying the mixture to provide the ifflaionic acid nanoparticles, wherein the alcohol solution is added dropwise to the boiled water at a flow rate of about 0.2 ml/min to about 0.4 ml/min.

2. The method of synthesizing ifflaionic acid nanoparticles according to claim 1, wherein the alcohol solution includes at least one of methanol and ethanol.

3. The method of synthesizing ifflaionic acid nanoparticles according to claim 1, wherein the ifflaionic acid nanoparticles have a size ranging from about 0.5 nm to about 10 nm.

4. The method of synthesizing ifflaionic acid nanoparticles according to claim 1, wherein the ifflaionic acid is obtained from *Nuxia oppositifolia.*

5. The method of synthesizing ifflaionic acid nanoparticles according to claim 4, wherein the ifflaionic acid is obtained from an n-hexane fraction of aerial parts of the *Nuxia oppositifolia.*

* * * * *